(12) United States Patent
Reddy et al.

(10) Patent No.: US 8,865,234 B1
(45) Date of Patent: Oct. 21, 2014

(54) TOPICAL PAIN RELIEVER

(71) Applicant: APPTEC, Inc., Cranbury, NJ (US)

(72) Inventors: Vilambi N R K Reddy, Cranbury, NJ (US); Anil Torgalkar, Cranbury, NJ (US); Regina A. Gallagher, Cranbury, NJ (US)

(73) Assignee: APPTEC, Inc., Cranbury, NJ (US)

( * ) Notice: Subject to any disclaimer, the term of this patent is extended or adjusted under 35 U.S.C. 154(b) by 0 days.

(21) Appl. No.: 13/967,312

(22) Filed: Aug. 14, 2013

(51) Int. Cl.
*A61K 36/00* (2006.01)
*A61K 36/889* (2006.01)
*A61K 36/47* (2006.01)
*A61K 36/61* (2006.01)
*A61K 36/534* (2006.01)
*A61K 36/24* (2006.01)
*A61K 31/045* (2006.01)
*A61K 31/618* (2006.01)
*A61K 36/53* (2006.01)

(52) U.S. Cl.
CPC ............... *A61K 36/24* (2013.01); *A61K 31/045* (2013.01); *A61K 31/618* (2013.01); *A61K 36/47* (2013.01); *A61K 36/53* (2013.01); *A61K 36/534* (2013.01); *A61K 36/61* (2013.01)
USPC ........... 424/725; 424/727; 424/731; 424/742; 424/747

(58) Field of Classification Search
None
See application file for complete search history.

(56) References Cited

U.S. PATENT DOCUMENTS

| | | | |
|---|---|---|---|
| 7,666,450 B2 * | 2/2010 | Reddy et al. | 424/725 |
| 8,399,030 B1 * | 3/2013 | Nur | 424/725 |
| 2006/0141061 A1 * | 6/2006 | Palpu et al. | 424/725 |

FOREIGN PATENT DOCUMENTS

| | | | |
|---|---|---|---|
| CN | 102283899 A | * | 12/2011 |
| CN | 102370947 A | * | 3/2012 |
| CN | 102631407 A | * | 8/2012 |
| DE | 202010010227 U1 | * | 11/2010 |
| RO | 122333 B1 | * | 4/2009 |
| WO | WO2012146194 A1 | * | 11/2012 |

OTHER PUBLICATIONS

Wilson et al. (Herbs used in Sidda medicine for arthritis, Indian Journal of Traditional Knowledge vol. 6(4), Oct. 2007, pp. 678-686).*

D. Ghosh, et.al,, "Anti-Inflammatory, Analgesic and Antipyretic Activities of 777 Oil—A Siddha Medicine," B.M E.B.R. vol. VI, No. 1 to 4, pp. 141-154 (see particularly pp. 143-144).

* cited by examiner

*Primary Examiner* — Chris R Tate
*Assistant Examiner* — Randall Winston
(74) *Attorney, Agent, or Firm* — Stanley H. Kremen

(57) ABSTRACT

Analgesic formulations to be applied topically that are reported to relieve moderate to severe pain due to tendonitis, fibromyalgia, shingles, insect bites and bee stings, ACL, arthritis, and sinus headaches. In many cases, test subjects report immediate pain relief with a single application and complete pain elimination with only a few applications. The formulations are in a coconut oil base which is skin friendly. The primary active ingredient is *wrightia tinctoria*, which when combined with other ingredients, causes the formulation to exhibit a synergistic effect on pain relief unexpected from using the ingredients alone or in combination.

6 Claims, No Drawings

TOPICAL PAIN RELIEVER

BACKGROUND OF THE INVENTION

An analgesic is a drug that relieves pain (analgesia). These "pain killers" are not anesthetics. Anesthetics reversibly eliminate sensation, while analgesics raise the level of sensitivity to pain. Analgesic medications may be administered intravenously, orally, or topically. When these medications enter the bloodstream or digestive tracts, there may be long-term side effects. Analgesic medications applied to the skin are generally safer than those administered internally.

Topical analgesics may be safely used to treat pain due to various conditions. Painful joints may be treated with a gel containing ibuprofen or diclofenac. Capsacin is also used to treat muscle aches. Salonpas® is a topically applied patch that uses capsacin to provide relief from mild pain due to arthritis, joint, hip, and back pain, as well as muscle aches. Lidoderm (5% patches) apply lidocaine (an anesthetic) to the affected area. Lidocaine is also used topically to relieve pain from mouth sores and to numb areas for dental work and minor medical procedures. Bengay is an analgesic heat rub used to relieve muscle and joint pain. The original Bengay contained 15% methyl salicylate and 10% menthol. The muscle pain, ultra-strength Bengay formula comprises 30% methyl salicylate, 10% menthol, and 4% camphor. Ice extra-strength Bengay contains 10% menthol. Muscle pain-no odor Bengay contains 15% triethanolamine salicylate. Arthritis extra-strength Bengay contains 30% methyl salicylate and 8% menthol. Other topical creams manufactured from minerals found in the Dead Sea are somewhat effective arthritis pain relievers.

777 Oil is an Indian topical medicine prepared from the leaves of *wrightia tinctoria*, a flowering tree found in India. The primary use for this plant is to formulate indigo dyes. The makers of 777 Oil proposed using it to treat various forms of psoriasis. In a reference by Ghosh, et. al., ("Anti-Inflammatory, Analgesic, and Antipyretic Activities of 777 Oil—A Siddha Medicine," B.M.E.B.D., Vol. VI No. 2 to 4 pp 141-184), the authors claim analgesic properties of the oil. Their conclusions were based upon their inducing a writhing response in mice by injecting them with acetic acid. In some of the mice, arthritis resulted from injections of formaldehyde. 777 Oil was then administered to these mice. The mice upon which the oil was administered were able to stretch more easily than the control group. The authors interpreted this response as analgesia. Unfortunately, these results are inconclusive, and not even suggestive of analgesia. While 777 Oil is used today for treatment of psoriasis, it is not used as a topical analgesic.

Many prescription and over-the-counter topical pain medications are currently sold in drug stores. Lidocaine is very effective when applied to mucous membranes. However, most preparations are effective only for mild pain. There is a long-felt and unfulfilled need for a topical application that would alleviate more severe pain.

SUMMARY OF THE INVENTION

The Present Invention is a group of formulations, comprising multiple ingredients which, when applied topically to a painful area, synergistically provides relief for more severe pain.

DETAILED DESCRIPTION OF THE INVENTION

The following formulation was tested on a number of subjects:

| | |
|---|---|
| *Wrightia tinctoria* extract | 30% |
| Coconut oil | 15% |
| Eucalyptus oil | 10% |
| Menthol | 10% |
| Clove oil | 5% |
| Peppermint oil | 10% |
| Methyl Salicylate | 20% |

The test subjects reported successful alleviation of mild to severe pain when applied topically. A coconut oil base was found to be desirable because it is very skin-friendly. A far more effective analgesic formulation is:

| | |
|---|---|
| *Wrightia tinctoria* extract | 30% |
| Coconut oil | 10% |
| Eucalyptus oil | 10% |
| Menthol | 10% |
| Clove oil | 5% |
| Peppermint oil | 10% |
| Methyl Salicylate | 5% |
| *Pergularia daemia* extract | 5% |
| *Vitex negundo* extract | 5% |
| *Clerodendron phlemoides* extract | 5% |
| *Recinus communis* extract | 5% |

The latter formulation was found to be very effective in alleviation of severe pain. Here also, the principal ingredient is *wrightia tinctoria* in a coconut oil base. However, the combination of ingredients in the latter formulation had an unexpected synergistic result. Several test subjects reported that severe forearm tendonitis (tennis elbow) was completely cured following five applications of the formulation over an eight hour period. Immediate relief from severe pain occurred with only one application. Other subjects applied the latter formulation to arthritic knees, and reported temporary relief from severe pain. Test subjects having severe sinus headaches applied the formulation to their foreheads, and the headaches disappeared instantly.

Both formulations have been found effective against pain from:
fibromyalgia,
shingles,
insect bites (not effective against mosquito bites),
bee stings, and
ACL.

Both formulations have been found effective to relieve inflammation and swelling (even post surgery).

The synergistic effect of combining the ingredients in both formulations was entirely unexpected. The above formulations fulfill a long-felt and unfulfilled need for a topical analgesic preparation that relieves mild, moderate, and severe pain.

We claim:

1. A topical pain formulation the ingredients of which comprise:
   a) *wrightia tinctoria* in an amount ranging between 20% and 40% by weight,
   b) coconut oil, and
   c) at least one of the following additional ingredients taken from the group consisting of:
   eucalyptus oil in an amount ranging between 8% and 15% by weight,
   menthol in an amount ranging between 2% and 15% by weight,
   clove oil in an amount ranging between 2% and 10% by weight, peppermint oil in an amount ranging between 5% and 12% by weight, and methyl salicylate in an amount ranging between 10% and 25% by weight, wherein, said formulation is prepared for topical application.

2. The topical pain formulation of claim 1 further comprising:
   a) *pergularia daemia* extract in an amount ranging between 2% and 20% by weight,
   b) *vitex negundo* extract in an amount ranging between 2% and 30% by weight,
   c) *clerodendron phlomoides* extract in an amount ranging between 2% and 40% by weight, and
   d) *ricinus communis* extract in an amount ranging between 2% and 10% by weight.

3. A topical pain formulation comprising:
   a) *pergularia daemia* extract in an amount ranging between 12% and 20% by weight,
   b) *vitex negundo* extract in an amount ranging between 15% and 30% by weight,
   c) *clerodendron phlomoides* extract in an amount ranging between 25% and 40% by weight, and
   d) *ricinus communis* extract
   wherein, said formulation is prepared for topical application.

4. A method for treating pain in a person, said method consisting essentially of:
   i) obtaining a formulation the ingredients of which comprise:
      a) *wrightia tinctoria* in an amount ranging between 20% and 40% by weight,
      b) coconut oil, and
      c) at least one of the following additional ingredients taken from the group consisting of
         *eucalyptus* oil in an amount ranging between 8% and 15% by weight,
         menthol in an amount ranging between 2% and 15% by weight,
         clove oil in an amount ranging between 2% and 10% by weight,
         peppermint oil in an amount ranging between 5% and 12% by weight, and
         methyl salicylate in an amount ranging between 10% and 25% by weight,
   ii) applying said formulation to the skin of the person.

5. The method of claim 4, wherein the additional ingredients of said formulation comprise:
   a) *pergularia daemia* extract in an amount ranging between 2% and 20% by weight,
   b) *vitex negundo* extract in an amount ranging between 2% and 30% by weight,
   c) *clerodendron phlomoides* extract in an amount ranging between 2% and 40% by weight, and
   d) *ricinus communis* extract in an amount ranging between 2% and 10% by weight.

6. A method for treating pain in a person, said method consisting essentially of:
   i) obtaining a formulation the ingredients of which comprise:
      a) *pergularia daemia* extract in an amount ranging between 12% and 20% by weight,
      b) *vitex negundo* extract in an amount ranging between 15% and 30% by weight,
      c) *clerodendron phlomoides* extract in an amount ranging between 25% and 40% by weight, and
      d) *ricinus communis* extract; and
   ii) applying said formulation to the skin of the person.

* * * * *